United States Patent [19]
Pistor

[11] 4,108,177
[45] Aug. 22, 1978

[54] AUTOMATIC INJECTOR DEVICE

[76] Inventor: Michel Louis Paul Pistor, 87, Boulevard Suchet, Paris, France, 75016

[21] Appl. No.: 787,142

[22] Filed: Apr. 13, 1977

[30] Foreign Application Priority Data

Apr. 23, 1976 [FR] France .................. 76 12126

[51] Int. Cl.² .................. A61M 5/00
[52] U.S. Cl. .................. 128/218 A; 128/DIG. 1
[58] Field of Search .......... 128/218 A, 218 F, 218 G, 128/218 R, 213, 215, 234, DIG. 1

[56] References Cited

U.S. PATENT DOCUMENTS

| 3,720,211 | 3/1973 | Kyrias | 128/218 A |
| 3,727,614 | 4/1973 | Kniazuk | 128/218 A |
| 3,768,472 | 10/1973 | Hodosh et al. | 128/218 A |
| 3,941,130 | 3/1976 | Tibbs | 128/218 A |
| 3,964,481 | 6/1976 | Gourlandt et al. | 128/218 A |

FOREIGN PATENT DOCUMENTS 909,898  11/1962  United Kingdom ............... 128/218 A

*Primary Examiner*—John D. Yasko
*Attorney, Agent, or Firm*—Flynn & Frishauf

[57] ABSTRACT

An automatic injector device operating stroke-by-stroke, comprising a frame whose shape is substantially similar to that of a revolver, a removable injection syringes comprising a syringe body, a syringe piston and at least one injection needle, a syringe-cradle carrying the said syringe and itself supported by the said frame, drive means on the one hand actuating in reciprocating motion the cradle-syringe assembly, and on the other hand actuating the syringe piston, and means for manually starting at least one injection, such as for example a trigger, which operates at least a part of said drive means.

12 Claims, 7 Drawing Figures

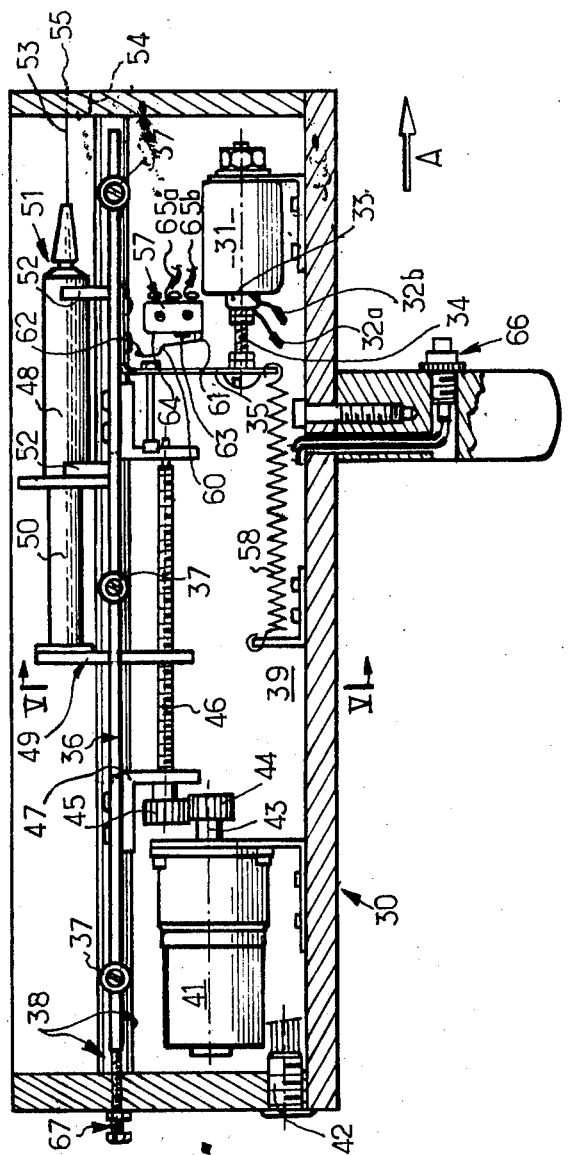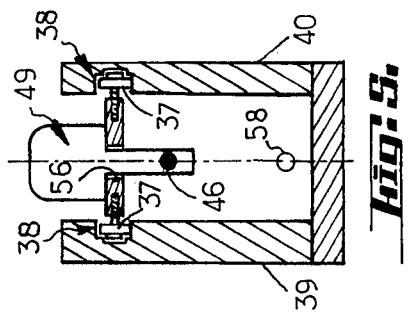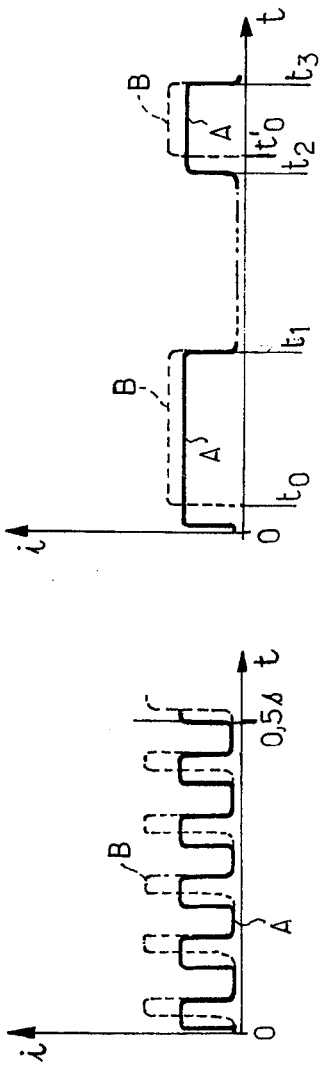

AUTOMATIC INJECTOR DEVICE

The present invention relates to an injection device having for an automatic injector capable of being operated either stroke by stroke, i.e., for carrying out injections one by one, successively, or in a continuous series of strokes, that is to say, so as to carry out at any desired rate a plurality of successive injections.

The device of the invention fills in a gap in the field of mesotherapy, where there are already available methods and implements allowing medicinal substances to be introduced into the system of persons and animals, such as for example multi-injectors allowing the carrying out of a plurality of simultaneous microinjections, and multi-puncture instruments which, by applying points or needles on the desired area of the skin, produce a microwound wetted by the treating product.

The new means proposed by the invention can be used to achieve more particularly the following purposes:

to perform mesotherapeutic treatments by carrying out injections either stroke by stroke or in a continuous series of strokes, at any desired rate;

to automate the said injection processes;

to provide apparatus characterized by high-speed and simplicity in operation, allowing a number of conventional steps to be dispensed with, such as those necessary for the reutilization of a specific syringe for further treatment, i.e. washing, unstoppering and sterilizing the syringes, which steps, as is known, are tedious owing to the labour involved.

The main advantages resulting from the invention are as follows:

possibility of making a great number of injections on a given area of the skin within a very short period of time, thus allowing the same amount of treating substance to be used more efficiently and therefore better results to be obtained than in the case of a single or only a few important injections;

high-speed and simplicity in operation as a result of automation and of the fact that means are provided for eliminating each injection syringe after its use and replacing it by a new injection syringe (use of disposable syringes, preferably of plastics and therefore not expensive).

SUMMARY OF THE INVENTION

The automatic injection device according to the invention is characterized in that it comprises a preferably pistol-, revolver- or like-shaped frame, a preferably removable injection syringe, comprising a syringe body, a syringe piston and a single injection needle or a multi-injector provided with a plurality of injection needles, a syringe cradle carrying said syringe and itself supported by said frame, drive means which on the one hand actuates in reciprocating motion either the cradle-syringe assembly or only the injection needle or the multi-injector with which the injection syringe is provided, and which on the other hand actuates the syringe piston or a movable member bearing on the latter, and manual means for starting at least one injection, such as for example a trigger, which operates all or part of the said drive means.

As is readily understood, it is necessary, in both stroke-by-stroke operation and series-strokes operation, to carry out injection cycles, each comprising:

a forward movement of the injection syringe so as to uncover the injection needle or needles which, in the position of rest of the device, are set back with respect to safety means, such as a protecting plate, the said forward movement allowing the needle or needles to penetrate through the skin; and then either a drive-in movement of the syringe piston into the syringe body, so as to perform the injection of the treating product followed by the return movement of the injection syringe (without displacement of the piston with respect to the syringe);

or directly, the above-mentioned return movement of the syringe during series-strokes operation without injection, mentioned earlier.

In a preferred form of embodiment of the invention, it is the assembly constituted by the syringe body, its cradle and the injection needle or needles that performs the said reciprocating or to-and-fro movement.

According to another feature of the invention, the injection device comprises first drive means actuating in reciprocating motion the cradle-syringe assembly and second drive means actuating the syringe piston or a movable member acting upon the latter.

According to another feature of the present invention, the injection syringe is removably mounted in the said frame, thus allowing each injection syringe to be replaced by a new syringe after the treatment of a given patient, so that the work can be carried out without useless complications and under the best conditions of sterility, using for example sterile syringes which, for economic reasons, are advantageously made of plastic and disposed of immediately after being used.

According to a preferred form of embodiment of the invention, the drive means for the reciprocating movement of the cradle of the syringe and the driving of the piston into the latter comprises, on the one hand, an electro-magnet actuating a magnetic core connected to a movable member bearing upon said piston and capable of driving in reciprocating motion towards its forward position corresponding to the injection, the syringe-cradle assembly and then only the said piston, owing to means for guiding the said cradle on the said frame and to stop means limiting the displacement of the said assembly with respect to said frame, and on the other hand, means for resiliently returning said assembly to its retracted rear position corresponding to the position of rest of the device.

According to a still more preferred form of embodiment of the invention, the device comprises means for guiding the cradle on the said frame, stop means for limiting the displacement of the said assembly with respect to the said frame and means for resiliently returning the said assembly to its retracted rear position, said first drive means comprises on the one hand an electro-magnet actuating a magnetic core capable of driving in rectilinear motion towards its forward position, corresponding to the injection, the syringe-cradle assembly, and said second drive means comprises an electric motor connected to the said movable member by a screw-and-nut transmission, the nut portion of which is constituted by the said movable member which is capable of driving the piston in rectilinear displacement towards its innermost position in the syringe body after the syringe-cradle assembly has been moved towards its forward position in which the said assembly is in contact with the said stop means.

Lastly, according to still another feature of the present invention, the device of the present invention comprises means for the supply of chopped direct current (or two chopped direct currents) to said drive means, which allows a continuous series of rapid injections to be obtained, each of the plateaus of the graph representing the intensity of the said chopped direct current as a function of time corresponding to the forward movement of the syringe-cradle assembly and, in case a second chopped direct current is provided, each of the plateaus of another graph representing the intensity of the said second chopped direct current as a function of time corresponding to the subsequent inward movement of the piston into the syringe body in case of product injection, whereas the or areas between the plateaus of the first-named graph correspond to the return movement of the said assembly under the action of the resilient return forces.

In case the drive means of the present invention are of the electromagnetic type, the electromagnet is advantageously placed within the said frame, e.g. within the grip portion or the body of a pistol- or revolver-shaped frame; where the aforesaid drive means includes an electric motor, the latter may be placed within a pistol- or revolver-shaped frame or casing, or it may be located outside the said frame or casing and connected to the latter by a flexible shaft. The invention also includes a combination of drive means, e.g. of the electromagnetic type such as an electromagnet with drive means, e.g. of an electric type, such as an electric motor, placed or not within the said frame.

BRIEF DESCRIPTION OF THE DRAWINGS

FIG. 4 is a sectional view of an automatic injector according to a second preferred embodiment of the invention which also is in the shape of a revolver;

FIG. 5 is a sectional view taken on line V—V of FIG. 4 of the syringe-cradle guiding means;

FIG. 6 shows graphs illustrating the variation, as a function of time, of the intensity of the direct currents supplied, on the one hand, to the electromagnet (graph in full lines A) and, on the other hand, to the electric motor (graph in dotted lines B) in a specific example of stroke-by-stroke operation, corresponding to two injections; and FIG. 7 shows graphs illustrating the variation, as a function of time, of the intensity of the currents supplied on the one hand to the electromagnet (graph A) and on the other hand to the electric motor (B) in the case of operation in a continuous series of rapid strokes with injection.

DETAILED DESCRIPTION

Figure 1:
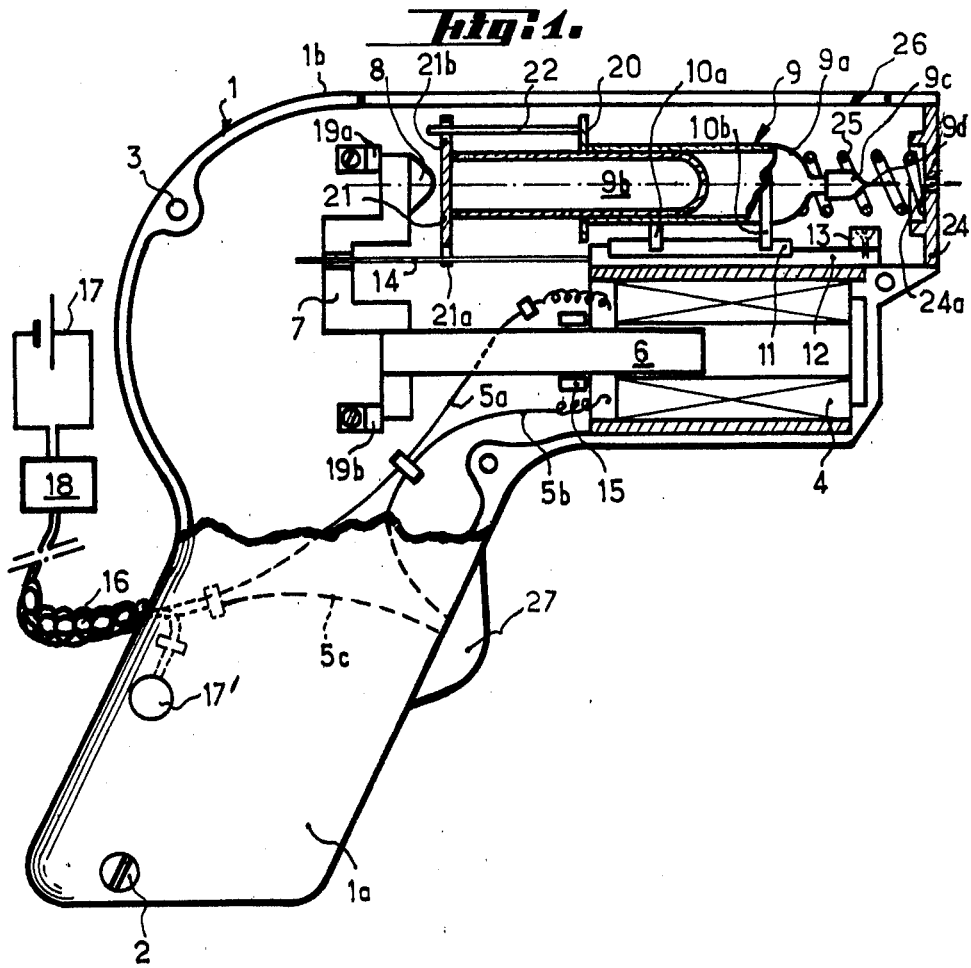
FIG. 1 is a partially sectional and partially external view of an automatic injector according to a preferred embodiment of the invention, which is shaped like a revolver.

The injector of FIG. 1 is essentially comprises a frame 1 in the shape of a revolver or the like, constituted by two half-casings 1a, 1b assembled together by means of screws such as 2 co-operating with tapped holes such as 3. The injector further includes a drive means comprising an electromagnet 4 supplied with power through conductors 5a and 5b and co-operating with a magnetic metal core 6 moving jointly with the movable member 7 provided with a bulge or the like forming a hammer 8. Further provided is an injection syringe 9, the body 9a of which is connected, through the medium of clamps or the like 10a and 10b gripping around the said body 9a, to a cradle or carriage 11 adapted to slide on a stationary rail 12 provided with a stop 13 limiting the forward displacement of the cradle 11, and with a guide rod 14 serving to guide the movable member 7 by co-operating with two guide half-rings such as 15 serving to guide the magnetic core 6. A trigger 27, when pressed, closes an electrical contact to supply the electromagnet 4 with current.

The conductors 5a, 5b and 5c connect to an external supply cord 16, which is connected to a source of direct current shown diagrammatically at 17. The injector also comprises an auxiliary operating member 17' such as a push-button, which, when actuated, switches on an appendant electronic device 18 of a type known per se converting the direct current supply of the source 17 into a chopped direct current which is fed to the electromagnet 4 when the trigger 27 is actuated.

Figure 3:
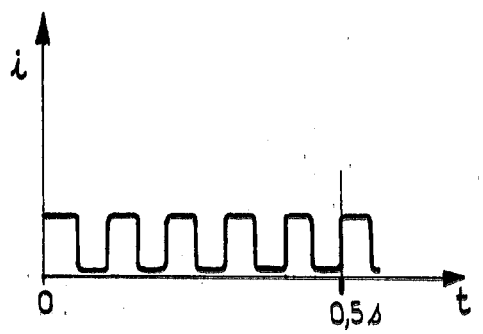
FIG. 3 is a graph illustrating the variation, as a function of time, of the intensity of a chopped direct current supplied to the electromagnet of the injector of FIG. 1, when the latter is operated in a continuous series of rapid strokes.

The wave-form of the said chopped direct current is shown in FIG. 3 where $i$ represents the intensity of the chopped current and $t$ is the time in seconds; in the example shown in FIG. 3 it is seen that the period of this chopped current is 1/10 of a second.

The stops 19a and 19b determine the rear retracted position of the assembly constituted by the magnetic core 6 and the movable member 7. The injection syringe 9 comprises a syringe body 9a ending with a flange 20, a syringe piston 9a provided with a rear flange 21 upon which the hammer 8 of the movable member 7 is adapted to bear, and an injection head 9c ending with an injection needle 9d as shown. In another embodiment of the invention, the head 9c may be replaced by a multi-injector provided with a plurality of small injection needles all of which are fed with treating substance from the syringe body 9a; the guiding of the piston 9b is ensured by the rod 14 passing through a peripheral notch 21a of the rear flange 21, and by a rod 22 connected to the flang 20 of the syringe body 9a and passing through an orifice 21b of the rear flange 21 of piston 9b. The frame 1 includes a removable end disc 24 provided with a central orifice 24a through which the injection needle 9d is adapted to pass, the infection needle being normally in retracted position, as shown, with respect to the outer surface of the said disc in the position of rest of the injector; a return spring 25 bears on the one hand upon the inner face of disc 24 and on the other against the end of the syringe body 9a.

The upper portion of the frame 1, i.e. the two half-casings 1a and 1b, is provided with an aperture 26 through which, after opening the clamps 10a and 10b to separate the syringe body from its cradle 11, the syringe as a whole can be removed in order to be replaced by a new syringe for a further treatment.

Figure 2:
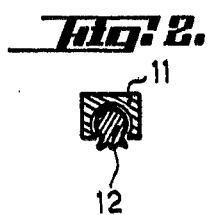
FIG. 2 is a sectional view upon II—II of the syringe-cradle guiding means.

FIG. 2 is a sectional view of the guiding means 11 and 12, from which it is seen that the cradle 11 cannot casually separate from its guide rail. In order to separate it therefrom it is sufficient, after taking off the disc 24, to remove the stop 13 screwed to the rail 12 and to cause the cradle 11 to slide forward and out of the barrel portion of the revolver-shaped frame 1.

The operation of the above injector can be described as follows: starting from the position of rest shown in FIG. 1, the feeding electrical power to of the electromagnet 4 causes the displacement of the assembly 6-7 towards the right, as a result of the electromagnetic attraction force exerted on the core 6; and the assembly constituted by the syringe and its cradle 11 performs a forward movement (i.e. a movement towards the right in FIG. 1), thus compressing the spring 25, until the front portion of the cradle 11 contacts the stop 13. The needle 9b thus reaches a position where it projects through the opening 24a beyond the outer surface of disc 24, and, since the disc 24 is applied on the skin, the needle 9d penetrates into the skin to the desired depth. The continuance of the forward movement of the assembly 6-7 results in driving the piston 9b into the syringe body 9a, thus causing the expulsion through the needle 9d of a given amount, determined by the constructional characteristics of the apparatus, of the treating substance contained in the syringe body 9a, thus performing the injection. When the pressure on the trigger 27 is removed, the feeding of electrical power to the electromagnet 4 ceases, thus allowing the return spring 25 to move the syringe body 9a back to its initial position shown in FIG. 1. A first cycle of injection corresponding to a single injection is thus accomplished. A new injection cycle may then be started, but the relative initial position of piston 9b is no longer the same as at the beginning of the first cycle, since it was driven into the syringe body 9a by a length corresponding to the amount of treating substance injected during the first cycle.

The stops such as 13 may be adjustable in position, allowing, if suitable, the travel of the syringe body 9a and the cradle 11 to be modified. The injection depth can thus be adjusted.

In stroke-by-stroke operation each new cycle is started by acting on the trigger.

In order to operate the injection device in a continuous series of rapid strokes, the operator first presses the push-button 17' so as to insert the appendant electric device 18 into the supply circuit of the electromagnet 4 when the trigger 27 is depressed and maintained in the depressed position. A chopped direct current is supplied to the electromagnet 4, allowing a series of injection cycles corresponding to a plurality of injections to be performed.

The injector of FIG. 4 comprises essentially a frame 30 whose walls are assembled for example by means of screws or the like, so as to be readily separable. First drive means are provided comprising an electromagnet 31 supplied through conductors 32a and 32b and cooperating with a magnetic metal core 33 connected by means of a rod 34 and a plate 35 to a cradle or carriage 36 adapted to move through the medium of wheels 37 on a rolling rail 38 provided to that end in the sidewalls 39, 40 of the frame 30 as seen clearly in FIG. 5. Second drive means are also provided, comprising an electric motor 41 supplied through conductors (not shown) leading to a supply socket 42 to which can be connected a supply cord. The motor 41 comprises a shaft 43 on which is mounted a gear wheel 44 meshing with a second gear wheel 45 driving in rotation a worm 46 constituting the screw portion of a screw-and-nut transmission and held in position by means 47 secured on the cradle 36, the movable member 49 constituting the nut portion of the said transmission. The movable member 49 is adapted to bear upon the piston 50 of a syringe 51 the body 48 of which is preferably removably secured on the cradle 36, e.g. by means of clamps 52. The syringe is provided with a single injection-needle 53 (or with a multi-injector carrying a plurality of injection-needles) which passes through an opening 54 provided in the frame 30 and the end 55 of which does not project beyond the frame 30 in the position of rest shown in FIG. 4.

The movable member 49 extends through the cradle 36 owing to a slot 56 (see FIG. 5) provided in the said cradle. This forward displacement of the carriage 36 (arrow A FIG. 4) is limited by stop means 57. The injector also comprises resilient return means 58 for the assembly constituted by syringe 51 and cradle 36 to its rear retracted position, as shown, the return means being connected to the plate 35 and the frame 30. It also comprises an electrical contact actuated at the end of the forward travel of the cradle-syringe assembly 36, 51 and starting the operation of the second drive means 41. This electrical contact preferably comprises a flexible metal element 60, one end (61) of which is attached to stop means 57 opposite the syringe-cradle assembly 51, 36, the free end 62 of the flexible element 60 being actuated at the end of the travel of the said assembly so as to apply the said element against a contact element 63 arranged at the surface 64 of the stop means 57. The contact element 63 is connected to conductors 65a, 65b leading to the second drive means 41.

The conductors 32a, 32b of the first drive means 31 are connected on the one hand to manual means for starting at least one injection, such as push-button triggering means 66, and on the other hand to the supply socket 42.

The travel of the cradle-syringe assembly 35, 51 towards its rear retracted position can be limited and adjusted by mechanical means such as an adjusting screw 67. The injector preferably comprises means, known per se, for the supply of two direct currents to the drive means 31 and 41 (graphs A and B of FIG. 6, respectively) so long as the operator maintains the trigger 66 depressed or for a predetermined period of time, or of two chopped direct currents, to the drive means 31 and 41 (graphs A and B, respectively, of FIG. 7), or of only one chopped current to the drive means 31 (graph A of FIG. 7).

The injector also preferably comprises means for pre-adjusting the length of rectilinear displacement of the syringe piston 50 towards its innermost position with respect to the syringe body 48. These pre-adjusting means adjust the rotary speed of the motor or, preferably, the duration of rotation of the said motor at constant speed. The said pre-adjusting means may comprise programming and time-delay means of a type known per se; use may also be made of an adjustable stop forming an electric contact (with possibility of switching out the motor 41) between the movable member 49 and a stop 57 slidingly mounted on the cradle 36.

The above injector operates as follows:

(a) Stroke-by-Stroke Operation (i) Continuous Injection (FIG. 6)

The trigger 66 is depressed, with the result of supplying direct current (graph A) to the electromagnet 31 and driving in rectilinear displacement towards its forward position (arrow A, FIG. 4) the syringe-cradle assembly until the said assembly contacts the stop means 57 through the medium of the flexible element 60 actuated against the contact element 63. The needle 53 has thus penetrated into the skin to the desired depth. The supply circuit of the motor 41 being closed owing to the contact between the flexible element 60 and the contact element 63, the motor 41 operates (at $t_0$) and drives in rectilinear displacement the piston 50 towards its innermost position with respect to the syringe body 48. This inward motion of the piston 50 therefore results in the expulsion of a given amount of the treating product contained in the syringe. The injection is stopped (at $t_1$) by removing the pressure on the trigger 66, which thus cuts the supply to the electromagnet 31. The resilient return means 58 then moves the cradle-syringe assembly 36, 51 back to its retracted rear position (FIG. 4) and the element 62 is no longer in contact with the contact element 63, thus cutting off the power supply to the electric motor 41. A second injection can be performed by again depressing the trigger, e.g. from a time $t_2$ to a time $t_3$ the duration of which is different, thus allowing the expulsion of a different volume of product (smaller duration and volume in FIG. 6).

(ii) Adjustable Predetermined Volume Injection

In this case use is made of the aforesaid means for preadjusting the length of rectilinear displacement of the syringe piston towards its innermost position with respect to the syringe body, and the electromagnet is supplied with power during the selected predetermined period following the actuation of the trigger 66.

(b) Operation in a Continuous Series of Strokes (i) Without Injection

In this case the motor 41 is switched off. Therefore, the piston 50 of the syringe 51 is not actuated by the movable member 49. The skin area to be treated is smeared with the treating product and then use is made of the means of supply of a chopped direct current to the electromagnet 31 (graph A, FIG. 7), the period of which may vary from 1/5 to 1/10 of a second, thus resulting in a series of reciprocating displacements of the cradle-syringe assembly 36, 51 and in prickings of the skin without injection.

(ii) With Injection (FIG. 7)

In this case use is made of the means for the supply of a chopped direct current to the electro-magnet 31 (graph A), the period of which may also vary from 1/5 to 1/10 of a second, for example 1/10 of a second (FIG. 7), and, as a result of the actuation of the contact means 60-63 for the supply of chopped direct current to the motor 41 (graph B). Consequently, there occurs a series of reciprocating displacements of the cradle-syringe assembly 36, 51 at a high rate with injection of product. The dose of injected product may also be pre-adjusted by using the means of pre-adjustment of the inward motion of the piston 50 of the syringe 51 as indicated in (a.ii) above.

Of course the arrangement of the drive means in the frame 30 as well as the shape of the frame may be modified. The upper portion of the frame is always provided with an opening to allow ready replacement of the injection syringe.

Of course, the invention is by no means limited to the embodiments described and illustrated which have been given by way of example only. In particular, it comprises all means constituting technical equivalents to the means described, as well as their combinations, should the latter be carried out according to its gist and used within the scope of the following claims.

What is claimed is:

1. An automatic injector device comprising:
   a frame;
   a removable injection syringe comprising a syringe body, a syringe piston and at least one injection needle;
   a syringe cradle carrying said syringe body and forming therewith a syringe-cradle assembly which is slidably mounted with respect to said frame by means of guiding means;
   drive means coupled to said syringe-cradle assembly for actuating said syringe-cradle assembly in reciprocating motion between a retracted rear position which is a non-operative position of said injector device and an operative front position corresponding to the injection position, and for actuating said syringe piston with respect to said syringe body;
   stop means located on said frame and delimiting said front position of said syringe-cradle assembly;
   said drive means including an electromagnet actuating a magnetic core connected to a movable member bearing upon said syringe piston, said drive means driving said syringe piston simultaneously with said syringe-cradle assembly in rectilinear displacement towards its front position and then only driving said syringe piston when said syringe-cradle assembly reaches its front position, said drive means further including resilient means for resiliently returning said syringe-cradle assembly to its retracted rear position; and
   control means for selectively energizing said electromagnet.

2. The injector device of claim 1 wherein said control means comprises a source of chopped direct current for supply to said electromagnet for repeatedly energizing said electromagnet for providing a continuous series of injections to be obtained as a result of a series of reciprocating displacements of said syringe-cradle assembly responsive to said energization of said electromagnet.

3. The injector device of claim 1 further comprising means for pre-adjusting the length of rectilinear displacement of said syringe piston towards its innermost position within the syringe body, thus allowing partial ejection of a predetermined volume to be performed.

4. The injector device of claim 1 wherein said control means comprises a source of direct current for supply to said electromagnet, said direct current being supplied permanently so long as an operator operates said control means.

5. The injector device of claim 1 wherein said control means comprises a source of direct current supply, and means for applying said direct current to said electromagnet for a predetermined period of time from the moment said control means is actuated by an operator.

6. An automatic injector device comprising:
   a frame;
   a removable injection syringe comprising a syringe body, a syringe piston and at least one injection needle;
   a syringe cradle carrying said syringe body and forming therewith a syringe-cradle assembly which is slidably mounted with respect to said frame by means of guiding means;
   drive means coupled to said syringe-cradle assembly for actuating said syringe cradle assembly in reciprocating motion between a retracted rear position which is a non-operative position of said injector device and an operative front position corresponding to the injection position, and actuating said syringe piston with respect to said syringe body;
   stop means located on said frame and delimiting said front position of said syringe-cradle assembly;
   said drive means including an electromagnet actuating a magnetic core connected to said syringe-cradle assembly for driving said syringe-cradle assembly in rectilinear displacement towards its front position, an electric motor, a screw rotatably driven by said electric motor and a movable member threadably connected to said screw and bearing upon said syringe piston, said screw and movable member comprising a transmission for driving said syringe piston in rectilinear displacement with respect to said syringe body, said drive means further including resilient means for resiliently returning said syringe-cradle assembly to its retracted rear position; and control means for selectively energizing said electromagnet and said electric motor.

7. The injector device of claim 6 wherein said control means comprises a source of chopped direct current for supply to said drive means for repeatedly energizing said electromagnet for providing a continuous series of injections to be obtained as a result of a series of reciprocating displacement of said syringe-cradle assembly responsive to said energization of said electromagnet.

8. The injector device of claim 6 further comprising means for pre-adjusting the length of rectilinear displacement of said syringe piston towards its innermost position within the syringe body, thus allowing partial injection to be performed.

9. The injector device of claim 6 wherein said drive means further comprises an electrical contact actuated at the end of the forward displacement of said syringe-cradle assembly and starting the operation of said electric motor.

10. The injector device of claim 9 wherein said electrical contact comprises a flexible metal element, one end of which is attached to said stop means opposite to the said syringe-cradle assembly and the other free end of which is actuated, at the end of said displacement of said syringe-cradle assembly, against a contact element provided at the surface of said stop means.

11. The injector device of claim 6 wherein said control means comprises a source of direct current for supply to said electromagnet, said direct current being supplied permanently so long as an operator operates said control means.

12. The injector device of claim 6, wherein said control means comprises a source of direct current supply, and means for supplying said direct current to said electromagnet for a predetermined period of time from the moment said control means is actuated by an operator.

* * * * *

UNITED STATES PATENT AND TRADEMARK OFFICE
CERTIFICATE OF CORRECTION

PATENT NO. : 4,108,177
DATED : August 22, 1978
INVENTOR(S) : Michel L.P. PISTOR

It is certified that error appears in the above-identified patent and that said Letters Patent are hereby corrected as shown below:

Column 4, line 45, change "infection" to --injection--;

line 66, change "the feeding electrical power to of" to --the feeding of electrical power to--;

Column 5, line 6, change "needle 9b" to --needle 9d--.

Signed and Sealed this

First Day of May 1979

[SEAL]

Attest:

RUTH C. MASON
Attesting Officer

DONALD W. BANNER
Commissioner of Patents and Trademarks